United States Patent [19]

Roland et al.

[11] Patent Number: 4,595,659

[45] Date of Patent: Jun. 17, 1986

[54] FERMENTATION PRODUCTION OF ASCORBIC ACID FROM L-GALACTONIC SUBSTRATE

[75] Inventors: John F. Roland, Glenview, Ill.; Theodore Cayle, Fox Point, Wis.; Robert C. Dinwoodie, Glenview; David W. Mehnert, Lake Villa, both of Ill.

[73] Assignee: Kraft, Inc., Glenview, Ill.

[21] Appl. No.: 543,975

[22] Filed: Oct. 20, 1983

[51] Int. Cl.⁴ .......................... C12N 1/32; C12P 7/62; C12P 7/60; C12R 1/72
[52] U.S. Cl. .................................... 435/135; 435/138; 435/247; 435/255; 435/921
[58] Field of Search ............... 435/135, 138, 247, 255, 435/921; 426/34, 41, 48

[56] References Cited

U.S. PATENT DOCUMENTS

| | | | |
|---|---|---|---|
| 3,809,611 | 5/1974 | Takayama et al. | 435/921 |
| 4,168,201 | 9/1979 | Wegner | 435/247 |
| 4,259,443 | 3/1981 | Danehy | 435/138 |
| 4,322,498 | 3/1982 | Takayama et al. | 435/921 |

FOREIGN PATENT DOCUMENTS 0533283 11/1956 Canada ............................ 435/921

OTHER PUBLICATIONS

Nishikimi, M. et al., *Archives of Biochemistry and Biophysics*, vol. 191, No. 2, Dec., pp. 479–486, 1978.
Heick, H. M. C. et al., *Canadian Journal of Microbiology*, vol 18, pp. 597–600, 1972.
Lodder, J., *The Yeasts*, North-Holland Publ. Co., Amsterdam, pp. 595–601, 1015–1018, 1970.
Stecher, Paul C. et al., *The Merck Index*, 8th Ed., Merck Co., Inc., Rahway, N.J., p. 786, 1968.
Bleeg, H. S. et al., *European Journal of Biochemistry*, 127, pp. 391–396, 1982.
Sanchez, J. et al., *Applied Microbiology and Biotechnology*, vol. 20, pp. 262–267, 1984.

*Primary Examiner*—Thomas G. Wiseman
*Assistant Examiner*—Elizabeth C. Weimar
*Attorney, Agent, or Firm*—Fitch, Even, Tabin & Flannery

[57] ABSTRACT

Processes for the fermentation production of L-ascorbic acid (Vitamin C), and to microorganisms (e.g., *Candida Norvegensis* MF-56, ATCC 20686) and fermentation media which are specifically adapted for such fermentation.

15 Claims, 1 Drawing Figure

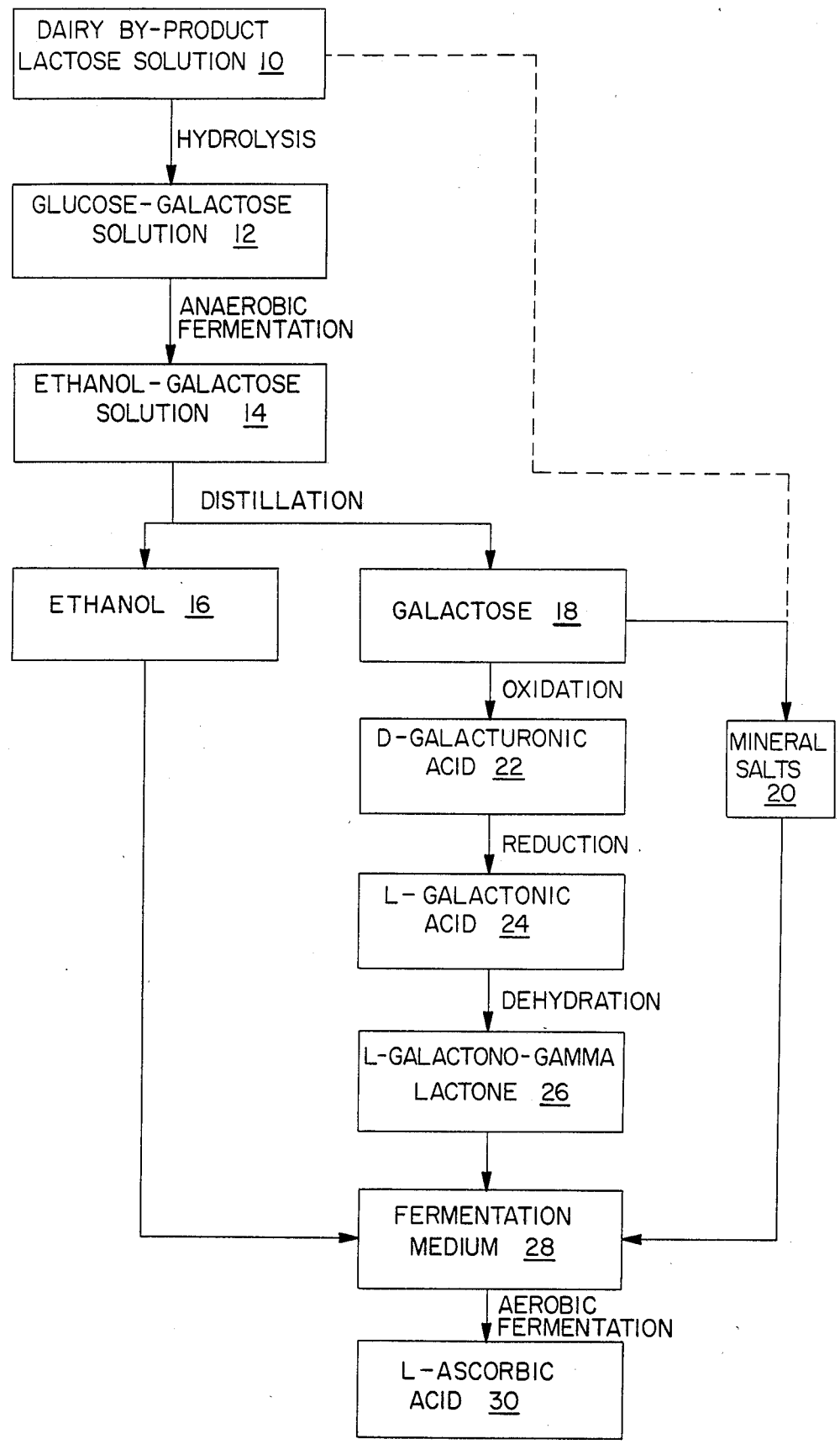

FERMENTATION PRODUCTION OF ASCORBIC ACID FROM L-GALACTONIC SUBSTRATE

The present invention relates to methods for the production of L-ascorbic acid (Vitamin C) by fermentation, and to microorganisms and fermentation media which are particularly adapted for such fermentation.

BACKGROUND OF THE INVENTION

L-ascorbic acid is an essential dietary component for man, and is naturally present in citrus fruits and plants. It is conventionally synthesized by a variety of known methods such as that described in U.S. Pat. No. 2,265,121 to T. Reichstein using D-glucose as the starting material. Various other chemical and biological methods are known for synthesis and manufacture of L-ascorbic acid, such as those described in U.S. Pat. Nos. 2,702,808, 2,847,421 and 3,721,663, which are generally variations of the Reichstein process. However, as indicated, these are relatively complex processes which utilize glucose as starting material. Novel commercial-scale processes which utilize other starting materials would be desirable.

As described in British Pat. No. 763,055, chemical-biological processes in which dehydrogenase (EC 1.3.2.3) present in enzyme animal or vegetable tissues is utilized to carry out terminal oxidation of the gamma lactones to provide L-ascorbic acid. A similar process is described in U.S. Pat. No. 4,259,433 in which hydrolyzed sugars of lactose and plant dehydrogenase enzyme (EC 1.3.2.3) derived from pea seedlings are utilized to produce L-ascorbic acid. The efficiency of the process was not disclosed but application at a commercial scale would appear to be restricted.

It has been recognized that bakers and/or brewers yeast contain L-galactono-lactone oxidase(s), an enzyme(s) believed to catalyze the terminal oxidation step in L-ascorbic acid biosynthesis in which the enzyme(s) catalyzes the oxidation of L-galactono-gamma lactone to produce L-ascorbic acid and hydrogen peroxide [*Enzymologia*; 31 #2 (1966), *Eur. J. Biochem.*; 127, 391 (1982) and others, M. Nishikimi, et al., *Arch. Biochem. Biphys.*, 191, 479 (1978)]. Studies of the ability of yeasts grown in a nutrient medium containing D-glucose (10%) as the carbon energy source to produce ascorbic acid analogs of the enediol class have also been carried out [Heick, et al., *Can. J. Microbiol.*, 18, 597 (1972)]. In a similar study, Candida yeast strains have also been grown on sucrose, hexose or pentose to produce an ascorbic acid analog (D-erythroascorbic acid) [S. Murakawa, et al., *Agric, Biol. Chem.*, 40 (6), 1255 (1976), 41 (9) 1799 (1977)]. When the yeasts were grown in the added presence of L-galactono gamma lactone, L-ascorbic acid was also identified. Although D-erythroascorbic acid was formed from a variety of carbon sources, L-ascorbic acid was only formed when the L-sugar-lactone was also present in the fermentation medium.

It is also known that a vast amount of lactose is available as a byproduct from cheese manufacture, in the form of whey, whey permeate or milk permeate. Utilization of these byproducts has long been a source of concern to cheese manufacturers.

It has also long been known that lactose obtained from whey or other fluid milk derived byproducts may be hydrolyzed to provide glucose and galactose (e.g., U.S. Pat. Nos. 2,826,502, 2,826,503, 2,749,242, 2,681,858) and it is known that whey may be fermented to provide ethanol (e.g., Food engineering, November, 1977 pp. 74–75; British Pat. No. 1,524,618). A new process for the manufacture of L-ascorbic acid which could be adapted to utilize dairy byproduct lactose would be particularly desirable.

Accordingly, a principal object of the present invention is to provide novel fermentation processes for producing L-ascorbic acid which may be carried out on a commercial scale. Another object of the present invention is to provide processes which may be adapted to utilize a dairy byproduct lactose source, such as whey, whey permeate or milk permeate in the manufacture of L-ascorbic acid. A still further object of the present invention is to provide microorganisms which are capable of producing L-ascorbic acid by aerobic fermentation of ethanol in the presence of various D- and L-galactose derivatives such as L-galactono-gamma-lactone. A further object is provision of fermentation media which are particularly adapted for the microbiological manufacture of L-ascorbic acid. These and other objects will become more apparent from the accompanying drawings and the following detailed description.

DESCRIPTION OF THE DRAWINGS

FIG. 1 is a process flow diagram of an embodiment of a method for manufacturing L-ascorbic acid from dairy byproduct lactose in accordance with the present invention.

DESCRIPTION OF THE INVENTION

Generally in accordance with the present invention, methods are provided for manufacture of L-ascorbic acid by the aqueous phase aerobic fermentation of an L-galactonic substrate selected from the group consisting of L-galactono-gamma-lactone, lower alkyl esters of L-galactonic acid, L-galactonic acid, and mixtures thereof. As will be discussed in more detail hereinafter, the L-galactonic substrate may be provided in any suitable manner, such as by oxidation of D-galactose and by hydrolysis of pectinaceous materials such as citrus pectin. L-galactono-gamma-lactone is the particularly preferred L-galactonic substrate. Further in accordance with such methods, a short chain carbon fermentation energy source which may be selected from the group consisting of ethanol, glycerol and mixtures thereof is utilized in the fermentation. Ethanol is the particularly preferred carbon source.

The selection and utilization of an appropriate microorganism for the aerobic bioconversion fermentation is an important feature of the present methods. In this regard, microorganisms are desirably provided in the fermentation medium which are overproductive in L-ascorbic acid synthesis and which accumulate L-ascorbic acid from an L-galactonic substrate. By an organism which is "overproductive in L-ascorbic acid bio-synthesis" is meant an organism which either through natural mutation or genetic manipulation is capable of enhanced production of L-ascorbic acid as a metabolite at levels of at least about 0.3 grams per liter of fermentation medium based on the total volume of fermentation broth.

As indicated, the production of L-ascorbic acid by fermenting ethanol in the presence of L-galactonic substrate by particular microorganisms is an important part of the present disclosure. Yeasts, and particularly selected yeasts of the genus Candida which are over productive in L-ascorbic acid formation from a L-galactonic substrate and which can utilize short chain carbon sources are particularly preferred. However, other suitable microorganisms (particularly including appropriately genetically modified microorganisms) such as yeast of other genera, such as Hansenula, Saccharomyces, Klyuveromyces, Debaromyces, Nadsonia, Lipomyces, Torulopsis, Kloeckera, Pichia, Schizosaccharomyces, Trigonopsis, Brettanomyces or Schwanniomyces may also be employed in some circumstances.

In accordance with various aspects of the present invention, the microorganisms utilized should be capable of utilizing ethanol as the principal carbon source in oxidative fermentation to carry out bioconversion of L-galactono-gamma-lactone to produce L-ascorbic acid in yields of at least about 1 gram per liter. However, the preferred microorganisms are mutants which belong to the genus Candida and which have the characteristics necessary for the production of L-ascorbic acid, further including characteristics such as active transport of product into the fermentation broth and enhanced ability to metabolize alcohol under aerobic conditions. However, in some instances, strains which accumulate significant amounts within the cell may be of value. Further, while ethanol is the particularly preferred carbon source, it is recognized that glycerol may serve as a fermentation carbon source for growth and production of L-ascorbic acid or other enediol compounds. The critical determinant for the selection of a carbon source is that it not be converted to an isomer of L-ascorbic acid. The yeast may be naturally occurring, artificially mutated or genetically engineered strains, particularly including those belonging to the genus Candida, provided they have the ability to produce and accumulate L-ascorbic acid.

Suitable mutants may be induced by conventional mutation procedures, such as exposure to ultraviolet (UV) rays, and/or chemical mutagens, such as N-methyl-N'-nitro-N-nitrosoguanidine, ethyl methane sulfonate, nitrous acid, acriflavin and caffeine. Hybridization of over-producing yeast strains using protoplast fusion or electrofusion to produce improved recombinants can be employed as can recombinant DNA technology. Further it is recognized that many genera of yeast can be induced to produce L-ascorbic acid or analogs under appropriate conditions. Such strains which are overproductive in ascorbic acid production may accumulate the bulk of the ascorbic acid within the cells so that it is not released until cellular autolysis occurs. However, for fermentation processes in which the L-ascorbic acid is most easily recovered from the fermentation medium, it is desirable for the microorganisms to transport the product into the medium.

Accordingly, a particular feature of the present disclosure is the provision of specific microorganism strains which do not retain the L-ascorbic acid product within the cell, but rather permit transport from the site of formation into the fermentation medium. It is believed that the enzymatic system which carries out the manufacture of L-ascorbic acid from the L-galactono-gamma-lactone substrate is associated with the yeast mitochondria. Accordingly, the L-galactono-gamma-lactone substrate must cross the cell wall from the fermentation medium, and further must be transported across the mitochondrial membrane. The L-ascorbic acid reaction product must similarly be transported across the mitochondrial membrane and the cell wall to enter the fermentation medium. To provide for accumulation of L-ascorbic acid in the fermentation medium, microorganism strains which have such desirable transport properties across the cell and mitochondrial membranes are provided. In this regard, particularly preferred embodiments of the present invention utilize selected yeast species and strains such as the Candida mutants described hereinafter, that actively transport the bulk of the L-ascorbic acid or analogs they produce into the fermentation medium during their tropophase and idiophase growth sequences. In accordance with the present invention, novel microorganisms are provided which are particularly adapted to aerobically oxidize an L-galactonic acid substrate, and particularly L-galactono-gamma-lactone, to produce therefrom and accumulate substantially only L-ascorbic acid. Particularly preferred are such microorganisms which have enhanced ability to metabolize ethanol under aerobic conditions and which have transport of L-ascorbic acid across cell and mitochondrial membranes so that the L-ascorbic acid is provided in the aqueous fermentation medium.

An example of a particularly preferred, artificially mutated yeast which produces and accumulates L-ascorbic acid when grown on an ethanol-containing standard fermentation medium ("SM-1") and a special glycine-containing medium ("glycine medium") each also containing 0.5% by weight L-galactono-gamma lactone, is *Candida norvegensis* Kraft, Inc. MF-56. This strain has been deposited with the American Type Culture Collection Rockville, Md. and has received culture identification ATCC 20686. This yeast is a mutant strain derived and isolated through a series of mutagenic processes from *Candida norvegensis* CBS 2145. The genealogy of this L-ascorbic acid over-producer, and L-ascorbic acid yields in both standard and glycine fermentation media, is provided in the following table.

TABLE I

| Geneaology of L-Ascorbic Acid Over-Producers from *Candida norvegensis* | | |
|---|---|---|
| | L-Ascorbic Acid Produced (grams/per liter) | |
| | SM-1 | Glycine Medium |
| *Candida norvegensis* | | |
| CBS 2145 (EMS) | 0.09 | 0.30 |
| MF-27 (UV) | 0.015 | 0.60 |
| MF-34 (UV/CAF) | 0.020 | 0.72 |
| MF-39 (UV) | 0.30 | 0.75 |
| MF-42 (NTG) | 0.30 | 0.69 |
| MF-54 (NA) | 0.33 | 0.75 |
| MF-55 (Ni$^{+2}$) | 0.34 | 0.80 |
| MF-56 | 0.34 | 1.07 |

Fermentations were carried out at 30° C. for 48 hours in low actinic 500 ml Erlenmeyer flasks containing 50 ml of the respective fermentation medium containing ethanol 1.5% w/v and L-galactono-gamma-lactone 0.5% (400 RPM). The mutation inducing agent from the previous strain is shown in parentheses, in accordance with the following abbreviations: UV=ultraviolet radiation; EMS=ethyl methane sulfonate; NTG=N-methyl-N'-nitro-N-nitrosoguanidine; NA=nitrous acid; CAF=caffeine; Ni$^{+2}$=Nickel L-galactonate.

The process of screening selection of over producing mutants for L-ascorbic acid may be carried out by applying mutagenic treatment to a large number of yeast cells, and subsequently selecting yeast colonies based on the level of ascorbic acid production. The level of ascorbic acid production may be monitored by culturing isolated cells of the mutagenicly treated yeast in a culture medium which is sensitive to acid production. For example, a culture medium may be opacified with an acid-sensitive material such as powdered calcium carbonate. Acid production by a growing yeast colony will dissolve the calcium carbonate, thereby providing a clarified zone surrounding the colony, the diameter of which increases as a function of increased yeast colony acid production.

Data for mutagenic treatment and screening in respect to one of the cultures in the geneology of Table I, designated as *C. norvegensis* MF-39 is set forth in the following Table II.

TABLE II

STRAIN SELECTION FOR L-ASCORBIC ACID PRODUCTION

| UV Exposure Time | Acid Units | | | | |
|---|---|---|---|---|---|
| | 0-1.0 | 1.0-1.5 | 1.5-2.0 | 2.0-2.5 | <2.5 |
| 0 seconds | 464/468 | 4/468 | — | | |
| (100% sur.) | 99.14% | .85% | — | | |
| 15 seconds | 300/313 | 8/313 | 5/313 | — | |
| (13.66% sur.) | 95.84% | 2.5% | 1.59% | — | |
| 30 seconds | 4433/4480 | 27/4480 | 18/4480 | 2/4480 | |
| (4.8% sur.) | 83% | 7% | 9% | .88% | |
| 45 seconds | 343/500 | 30/500 | 108/500 | 18/500 | 1/500 |
| (.52% sur.) | 68.6% | 6% | 21.6% | 3.6% | .20% |
| 60 seconds | 30/37 | — | 6/37 | 1/37 | — |
| (.03% sur.) | 81.08% | — | 16.21% | 2.7% | — |
| 75 seconds | 277/288 | 7/288 | 2/288 | 1/288 | 1/288 |
| (0.1% sur.) | 96.18% | 2.43% | .69% | .34% | .34% |

In the work described by Table II, superior producing mutants were screened on the basis of their acid unitage (AU). In this regard, following mutagenic treatment the parent strain and the survivors were plated on an acid indicating medium, which was SM-1 culture medium containing Agar, ethanol 1.5% w/v, 0.5 L-galactono-gamma-lactone and mono-sodium glutamate 0.2%, further containing 0.3% Ca $CO_3$ as an opacifying agent, and incubated for 96 hours at 30 C. to determine their AU values. By AU values is meant the diameter of clear zone (mm)/diamer of colony zone. In Table Ii, the mutagenic U.V. exposure time is given in the first column of the table for exposure times of 0, 15, 30, 45, 60 and 75 seconds with the total survival percentage culture at that exposure time being shown thereunder. For each exposure time, the number fraction and percentage of surviving colonies are shown for each of the five different zone sizes of acid unitage, in respective columns of the table. Shake flask testing as described in Table I is used for productivity evaluations. The MF-42 strain was selected from among the mutated strains having highest acid unitage.

The morphological, culturaal and physiological characteristics of the mutant strain *C. norvegensis* Kraft, Inc. MF-56 and the parent strain *C. norvegensis* CBS 2145 are consistent with the yeast description provided in The Yeasts, a taxononomic study (J. Lodder (Ed.) 1970, North Holland Publishing Co., Amsterdam) and A New Key to the Yeasts (J. A. Barnett and R. J. Parkhurst (Ed) 1974, North Holland Publishing Co., Amsterdam). Morphological and identification tests are presented in Table III.

When grown on malt extract at 25° C., cells are cylindrical to ovoid (2-8)×(5-13) microns. Colonies are cream colored, glistening, soft and smooth. Ascospores are not formed on Folwells acetate agar.

TABLE III

Assimilation of carbon

TABLE III-continued

| compounds: | | | |
|---|---|---|---|
| Glucose | + | Ethanol | + |
| Galactose | — | Methanol | — |
| L-Sorbose | — | Glycerol | + |
| Sucrose | — | Erythritol | — |
| Maltose | — | Ribitol | — |
| Cellobiose | + | Galactinol | — |
| Trehalose | — | D-Mannitol | — |
| Lactose | — | D-Glucitol | — |
| Melibiose | | -Methyl-D-glucoside | — |
| Raffinose | — | Salicin | +/— |
| Melezitose | — | Arbutin | +/— |
| Insulin | — | DL-Lactic Acid | + |
| Soluble Starch | — | Succinic acid | + |
| D-Xylose + latent or | — | Citric acid | + |
| L-Arabinose | — | Inositol | * |
| D-Arabinose | — | Glucono-delta-lactone | — |
| D-Ribose | — | 2-Keto-gluconate | — |
| L-Rhamnose | — | 5-Keto gluconate | — |
| | — | D-Glucosamine | + |

Assimilation of $KNO_3$: negative
Growth without added vitamins: negative; thiamine, biotin and pyridoxone are required
Maximum temperature for growth: 41-45° C.

*sometimes weak

Another feature of the present invention is provision of aqueous fermentation media and fermentation conditions under which metabolic processes of gluconeogenesis from ethanol may be repressed and formation of D-erythroascorbic acid may be minimized. Particularly preferred aqueous fermentation media may be provided which facilitate the recovery of L-ascorbic acid and which enhance the microbiological production of L-ascorbic acid. The provision of an appropriate aqueous fermentation medium is a further important feature of methods in accordance with the present invention, and selection and provision of a desired fermentation medium is in part a function of the particular microorganism utilized in the fermentation. The provision of an appropriate fermentation medium may also provide for more effective L-ascorbic acid recovery procedures by separation techniques including ion exchange resin separation methods, as will be discussed in more detail hereinafter.

Ethanol is used as the carbon source in the fermentation medium and the initial concentration is preferably in the range of about 0.01-2.0% weight (grams)/volume (milliliters) herein "w/v" depending upon the particular strain employed. As ethanol is consumed during the fermentation it may be intermittently supplemented to give an optimum concentration (about 0.01%-2.0% w/v) which can be tolerated by the yeast and does not inhibit growth or L-ascorbic acid production.

In accordance with various aspects of such methods, an aqueous fermentation medium is provided comprising a carbon fermentation energy source having less than four carbon atoms selected from the group comprising ethanol, glycerol and mixtures thereof, an L-galactonic substrate selected from the group consisting of L-galactono-gamma-lactone, L-galactonic acid, and mixtures thereof. The fermentation medium will generally further contain nutrients necesssary for growth of the selected microorganism and will preferably have a pH in the range of from about 2.5 to about 6.5. Generally, at least about 0.01 weight percent, and preferably from about 0.1 to about 2.0 weight percent of the carbon source will be provided in the aqueous fermentation medium, based on the total weight of the fermentation medium. The carbon source is consumed during the fermentation and may be periodically or continously added during the course of the fermentation. Similarly, at least about 0.1 weight percent of the fermentation substrate will desirably be provided in the fermentation medium based on the total weight of the medium. For yeast fermentations, the fermentation medium will generally include a nitrogen source, various organic nutrients, and various minerals.

The nitrogen source (which may typically be utilized in an amount of about 0.1 to about 0.5 weight percent based on the total weight of the aqueous fermentation medium) may be selected from the group metabolizable nitrogen compounds comprising ammonium sulfate, ammonium nitrate, ammonium chloride or ammonium phosphate, urea or ammonium ion in the form of ammonium hydroxide, etc. and mixtures thereof, depending on the ability of the particular strain to best utilize the nitrogen source. Further, various amounts of organic nutrients such as amino acids (e.g., monosodium glutamate, glutamine, aspartic acid, etc.) or purines (adenine, thymine) corn steep liquor, yeast extract, protein hydrolysates etc., inorganic salts, such as, sulfates or hydrochlorides of Ca, Mg, Na, K, Fe, Ni, Co., Cu, Mn, Mo, Zn; vitamins (e.g., water soluble B vitamins) may be added to prepare a culture or fermentation medium. One such medium which effectively carries out this function is the previously referred to SM-1 ethanol medium. The compositional characteristics of this medium are listed as follows:

| SM-1 MEDIUM | | | Amount G.L.$^{-1}$ |
|---|---|---|---|
| A. | carbon - ethanol (weight/volume) | | 15.0 |
| B. | nitrogen - urea | | 2.0 |
| C. | Supp mix - corn steep liquor | | 5.0 |
| D. | Inorganic | | |
| | Salts - | $K_2HPO_4.3H_2O$ | 1.0 |
| | | $KH_2PO_4$ | 3.0 |
| | | $MgSO_4.7H_2O$ | 0.5 |
| | | NaCl | 0.1 |
| | | KCl | 0.1 |
| | | $H_3BO_3$ | .0005 |
| | | $FeCl_3.6H_2O$ | .0002 |
| | | $MnSO_4H_2O$ | .0004 |
| | | $ZuSo_4.5H_2O$ | .0004 |
| | | $CUSO_4.5H_2O$ | .0004 |
| | | KI | .0001 |
| | | $(NH_4)_6MO_7O_{24}.4H_2O$ | .0002 |
| E. | Vitamins - | Thiamine HCl | .004 |
| | | Biotin | .00002 |
| F. | Bioconversion Compd. L-galactono-γ-Lactone | | 5.0 |
| G. | Adjust to pH 4.0 | | |

When selected mutant yeast are grown in this medium under appropriate cultural conditions essentially only L-ascorbic acid is produced as the bioconversion product of L-galactono-gamma-lactone provided in the culture medium. Modifications of this medium or other media (as will be more fully discussed hereinafter) may prove to be more beneficial. The conditions for culturing are typically a temperature in the range of from about 20° C. to about 37° C. and preferably about 30° C. The fermentation is desirably carried out at a pH in the range of from about 6.5 to about 2.6 and preferably about 4.0. The optimum conditions will depend on the particular yeast strain employed. The fermentation process may take from 1 to 7 days and is operated under aerobic conditions. When a high density yeast cell biomass (range 25-240G/WTCWT) is employed in the bioconversion process to produce L-ascorbic acid, the additional supplementation of pure oxygen or an oxygen enriched atmosphere to the aeration process may be required to prevent the development of anaerobic conditions or may be desirable to enhance yields. It is desirable that at least about 2.5 ppm oxygen be maintained in the aqueous culture medium, and preferably the oxygen content should not decrease below a predetermined level in the range of from about 3 to about 5 ppm.

While standard culture media such as the SM-1 culture medium previously described may advantageously be utilized in the manufacture of L-ascorbic acid from a L-galactono-gamma-lactone substrate in accordance with the present invention, it is particularly preferred that the fermentation be carried out utilizing a culture medium of at least about 0.5 weight percent and preferably in the range of from about 0.6 weight percent to about 0.8 weight percent glycine, based on the total weight of the culture medium. It has been found that about 0.7 weight percent glycine in the medium is particularly effective in respect to yield enhancement. In this regard, it has been found that such high glycine culture media appear to enhance the yield productivity of L-ascorbic acid by factors of about 3 or more. The components of a glycine fermentation medium which has proven to be particularly effective in the fermentations described herein, and which are identified herein as "glycine medium" are listed as follows:

| GLYCINE MEDIUM | |
|---|---|
| component | amount (grams per liter) |
| Ethanol | 20.0 |
| Glycine | 7.0 |
| CSL w,v | 5.0 |
| mono sodium glutamate | 2.0 |
| $NH_4Cl$ | 1.0 |
| $MgSO_4$ | 0.5 |
| mineral mix | 2.0 ml |
| The mineral mix consists of: | |
| EDTA (2Na) | 5.0 grams per liter |
| $ZnSO_4.7H_2O$ | 0.22 grams per liter |
| $CaCl_2.2H_2O$ | 0.735 grams per liter |
| $MnSO_4.H_2O$ | 0.6725 grams per liter |
| $FeSO_4.7H_2O$ | 0.915 grams per liter |
| $(NH_4)_6Mo_7O_{24}.4H_2O$ | 0.10 grams per liter |
| $CuSO_4.5H_2O$ | 0.25 grams per liter |
| $CoCl_2.6H_2O$ | 0.293 grams per liter |

As will be more fully described, the L-galactonic substrate may desirably be manufactured from cheese or dairy byproduct lactose by hydrolyzing the lactose to produce glucose and D-galactose and oxidizing the D-galactose to produce D-galacturonic acid:

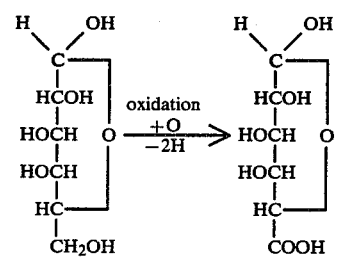

D-galacturonic acid may also conveniently be provided by hydrolysis, such as enzymatic hydrolysis, of pectinaceous materials such as citrus pectin. The D-galacturonic acid may be reduced to provide L-galactonic acid, which may be dehydrated to form L-galactano-gamma-lactone:

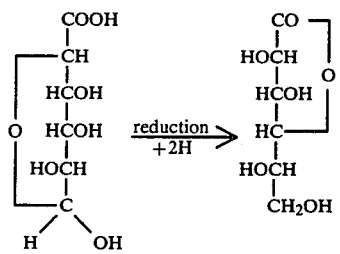

VArious derivatives of L-galactonic acid particularly including the lower alkyl esters may be manufactured by conventional esterification reaction of L-galactonic acid:

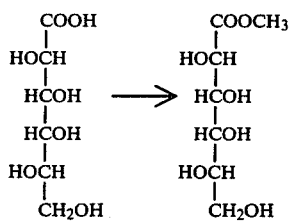

In accordance with the method, aerobic fermentative conditions are maintained under which the substrate is oxidized by the microorganism to substantially only L-ascorbic acid produced by the microbiological oxidation. The L-ascorbic acid produced by the aerobic fermentation may be subsequently recovered in an appropriate manner, as will be more fully described.

It is necessary to maintain aerobic conditions during the fermentation, and in this regard, it is desirable that at least 20% (e.g., 20–30% oxygen-saturation (e.g., 2–3 ppm of oxygen) be maintained in the aqueous fermentation medium during the fermentation. Maintaining aerobic conditions may be carried out by introducing oxygen enriched gas into a fermentation medium, and by utilizing fermentation equipment, such as air lift reactors, which effectively disperse oxygen into the fermentation medium.

As indicated, ethanol may be utilized as the principal carbon energy source under fermentation conditions in which L-galactono-gamma-lactone is substantially wholly converted to L-ascorbic acid. For example, when Candida yeast are grown on ethanol (a 2-carbon energy source), employing SM-1 -medium and 0.5 weight percent L-galactano-gamma-lactone rather than on hexose sugar (6-carbon energy source) as the energy source in SM-1 medium with 0.5% L-galactono gamma-lactone essentially only L-ascorbic acid is formed and production of other ascorbic acid analogs, e.g., D-erythroascorbic acid is minimized. This is an important factor in the development of a practical process to produce L-ascorbic acid at levels of industrial interest.

The fermentation process is a bioconversion process in which L-galactono-gamma-lactone is converted to a structurally related product by one or a small number of enzymes within a cell. The process may be carried out using growing cells, resting vegetative cells, dried cells or cells immobilized in various organic polymers, such as K-carrageenan, polyacrylamide, gelatin, or agar, or other macroporous resins or inorganic compounds, such as cordierite and silica.

The L-ascorbic acid bioconversion process may be operated in conventional aerobic fermentation modes, e.g., batch, continuous, semi-continuous. Also cultivation methods usable to obtain high-density of biomass; dialysis culture, semi-batch with cell separator and fed-batch processes may be employed in which oxygen supplements to air may be required.

Having generally described the present invention, various aspects thereof will now be more particularly described with respect to the process embodiment illustrated in block diagram by FIG. 1.

FIG. 1 is a schematic illustration of an embodiment of a process for manufacturing L-ascorbic acid from a dairy by product lactose solution substrate 10 such as whey, whey permeate or milk permeate. The dairy fluid lactose solution may typically comprise from about 4.5 to about 5.0 weight percent lactose, which is hydrolyzed to provide its constituent sugars, glucose and galactose in the form of glucose-galactose solution 12. The hydrolysis may be accomplished in a conventional manner using a lactase enzyme derived from a yeast (*K. fragilis* or *K. lactis*) or a mold enzyme derived from *A. niger* or *A. oryzae*. The enzyme may be employed either in a free, entrapped or immobilized form.

The glucose-galactose solution 12 or the lactose solution 10 may be deproteinized or demineralized in accordance with conventional procedures if necessary or desirable in carrying out the alcohol fermentation. The glucose-galactose solution provided by the hydrolysis treatment step may be concentrated to provide a solution comprising for example in the range of from about 15 percent to about 30 percent by weight, based on the total weight in the solids solutions. The non-lactose solids content may typically be in the range of from about 0.5 to about 1.0 weight percent of the total solids, such that the total glucose and galactose content of the solution may desirably be in the range of from about 20.0 to about 22.5 percent by weight based on the total weight of the solution.

After supplementation with suitable nutrients such corn steep liquor or yeast extract in accordance with conventional yeast fermentation procedures, the glucose-galactose solution 12 may be fermented under anaerobic conditions using an appropriate yeast strain for fermentation of glucose to ethanol, such as a selected yeast strain of *S. cerevisiae*, in order to convert the glucose to ethanol and carbon dioxide without substantially consuming the galactose component of the fermentation medium. In this manner an ethanol-galactose solution 14 is provided.

The ethanol-galactose fermentate may typically comprise at least about 5 percent ethanol on a weight to volume basis, and at least about 10 weight percent D-galactose based on the volume and weight of the fermentation 14 respectively. The fermentate 14 is distilled to remove the alcohol 16 which may subsequently be rectified to provide 190 proof grain alcohol, if desired. This alcohol 16 may then be utilized in the L-ascorbic acid fermentation process to serve as carbon energy for the selected microorganism utilized in the fermentation.

In this regard, the stillage containing D-galactose recovered after removal of ethanol may be concentrated further by appropriate methods to provide a galactose solution having a total solids content in the range of from about 20 to about 75 weight percent based on the total weight of the solution, and which may desirably contain from about 16 to about 62 weight percent of galactose based on total solution weight. This galactose solution may be crystallized to obtain purified D-galactose 18. The mineral salts 20 may be utilized in the L-ascorbic acid fermentation, if desired; as a supply of inorganic nutrients for the fermentation medium. Alternatively the galactose may be separated from the rest of the fermentation components via ion exclusion. Such galactose can serve directly as the feedstock for reaction step 18.

The D-galactose 18 is converted by catalytic oxidation to provide D-galacturonic acid 22. Processes to carry out this oxidative step for D-sugar acids are well known in the art and have been described in U.S. Pat. No. 2,265,121 by T. Reichstein. A variety of catalytic agents, e.g., platinum or palladium catalysts may be employed to convert blocked D-galactose (acetone) to the D-galacturonic acid product. The unblocked D-galacturonic acid may then be reduced by an appropriate reduction step such as reduction with gaseous hydrogen in the presence of a suitable hydrogenation catalyst such as Raney nickel, or palladium, to produce L-galactonic acid 24. Processes to carry out this chemical reduction are well known in the art such as described by H. Isbell, *J. Res. Nat. Bur. Stds.*, 33, 45–60 (1944) Removal of water by distillation and condensation of the desalted L-sugar acid induces the formation of L-galactono-gamma-lactone 26 which is utilized in the microbiological conversion process of the present invention to form L-ascorbic acid. Other galactose derivatives such as L-galactonic acid esters and L-galactonic acid may be utilized although yields of L-ascorbic acid are reduced due to less efficient utilization. Keto-derivatives such as 5-Keto-L-Galactonic acid, are not utilized by the preferred yeast strains particularly described herein. The L-galactono-gamma-lactone 26, ethanol 16, and suitable organic and inorganic nutrients are combined to provide a fermentation medium 28 for a selected L-ascorbic acid overproducer.

The L-ascorbic acid fermentation process may be carried out in conventional stirred aerated fermentors such as a 30 liter New Brunswick Scientific fermenter. Monitoring of product formation and control of the cellular environment using physical and chemical sensors linked to a microcomputer may be carried out by means of detectors for measuring ethanol, pressure, an input flow, exhaust gas, carbon dioxide, exhaust gas oxygen, pH, and dissolved oxygen.

After cultivation, L-ascorbic acid 30 produced by the fermentation may be recovered from the clarified fermentation broth by a variety of methods such as by using ion exchange resins, absorption or ion retardation resins, activated carbon, concentration-crystallization, etc.

The course of the fermentation may be monitored by appropriate analytical procedure. Quantitative assay of L-ascorbic acid and analogs may be carried out using redox-titration with 2,6 dichloroindophenol [N. G. Burton, et al., *J. Assoc. Pub. Analysts*, 17, 105 (1979)] and high-performance liquid chromatography using anion exchange [*J. Chrom.*, 196, 163 (1980)] and electro-redox procedures. [L. A. Pachia, *Anal. Chem.*, 48, 364 (1976)]. Enzymatic procedures involving the use of ascorbic acid oxidase (Boehringer-Mannheim) may also be employed.

The fermentation may be terminated when maximal production of L-ascorbic acid has been attained in the fermentation broth. Unconverted portions of L-galactono-gamma-lactone may be recycled.

Various aspects of the present invention will be further described with respect to the following specific examples, which are not intended to limit the scope of the invention.

EXAMPLE I

A stirred batch fermentation to produce L-ascorbic acid was carried out in a 30-Liter New Brunswick stirred fermentor. Fifteen liters of glycine medium composed of 0.25% corn steep liquor, 0.1% ammonium chloride, 0.7% glycine, 0.05% magnesium sulfate. $7H_2O$, 0.2% monosodium glutamate, 1.5% w/v ethanol and 0.30 ml of trace mineral mixture, was adjusted to pH 4.2 and sterilized for 30 minutes at 121° C. (Unless otherwise indicated values herein are in weight percentages). After cooling, 0.5% of cold-sterilized L-galactono-gamma-lactone was added to the sterile fermentation broth. The fermentor was inoculated with 500 ml of a 24 hour SM-1 broth culture of *C. norvegensis* KCC MF42 (Table I) grown in a 2-liter Erlenmyer flask on a rotary shaker at 30° C., 200 RPM.

The fermentor was operated at 30° C., 250 RPM and an aeration rate of 0.25 vol/vol/min. with the pH initially maintained at 4.0. After 24 hours, the supernatant broth contained 0.084 $GL^{-1}$ of L-ascorbic acid. An additional 27.0 mg was present in the yeast cells. After 48 hours the clarified broth contained 0.43 $GL^{-1}$ of L-ascorbic acid and the cells contained 29.6 mg. $L^{-1}$. The product could be recovered using conventional ion exchange resin absorption and elution followed by decolorization, evaporation and crystallization.

EXAMPLE II

A system of process intensification using high density biomass and product recovery was developed for the production of L-ascorbic acid using Candida yeast and mutants. In this procedure KCC MF-42 yeast cells were cultivated in SM-1 medium (ETOH 1.5% w/v) (L-Galactono-gamma-lactone 0.1%) for 18 hours in a stirred fermentor and centrifuged under sterile conditions. The cell paste provided by centrifugation was then aseptically reconstituted at 37.5 g $L^{-1}$ wet cell weight in sterile fresh SM-1 medium, pH 4.0 (Ethanol 1.5%—monosodium glutamate 0.2%—L-galactono-gamma-lactone 0.5%) and aerated with oxygen at a dissolved oxygen level of 65% of saturation. Production of L-ascorbic acid rose to 0.470 $GL^{-1}$ in 24 hours and increased to 0.580 $GL^{-1}$ in 45 hours. The pH of the medium dropped to 2.6 during the fermentation.

Four liters of chilled, clarified fermentation broth were passed through a 500 ml column of IR120 ($H^+$) resin, an ion exchange resin manufactured by Rohm and Haas. The effluent and washwater were collected and evaporated to 100 ml volume at 37° C. under vacuum. One hundred milliliters of cold ethanol was added and the precipitate (protein) was removed by centrifugation at 5000 RPM at 5° C. The product was again evaporated to 25 ml volume and stored at 0° C. for five days until crystallization was complete. The filtered crystals were washed 3 times with acetone, redissolved in warm alcohol and recrystallized. About 1.4 g of crude L-ascorbic acid crystals (HPLC) were recovered in the first crop.

Recovery and purification can also be carried out by absorption of L-ascorbic acid from broth on anion retardation resin (Dowex 1 type), acetic form and elution with 0.1M $H_2SO_4$.

EXAMPLE III

A process was developed in which resting cells of Candida yeast and mutants were used to produce L-ascorbic acid from ethanol and L-galactono-gamma-lactone in buffered salt solution. Both ethanol and L-sugar lactone are required by the yeast. The resulting cells may be used in a free state or immobilized in various polymeric gels or attached to polymeric resins, or inorganic mineral compounds.

In this example, yeast cells *Candida norvegensis* CBS #1911 cultivated 18 hours in SM-1 medium were centrifuged, washed in phosphate buffer (pH 4.5) and resuspended at a level of 3.0 grams wet cell weight/50 ml of 0.03% phosphate buffer solution (pH 4.5) containing 0.8% ethanol and 0.5% L-galactono-gamma-lactone. The 50 ml mixture in a 500 milliliter low-actinic, borosilicate Erlenmeyer flask was placed on a rotary shaker and aerated at 300 RPM at 30° C. Broth samples were taken periodically in order to monitor ethanol utilization and L-ascorbic acid production. Additions of ethanol were made periodically to maintain the alcohol concentration at about 0.3% w/v concentration. Results of the L-ascorbic acid accumuation by the yeast after 96 hours are shown in TABLE IV:

TABLE IV

| Microorganism used C. Norvegensis CBS - #1911 | L-ascorbic acid accumulated (mg $L^{-1}$) | Time Hours |
|---|---|---|
| | 90 | 33 |
| | 130 | 48 |
| | 200 | 73 |
| | 260 | 96 |

EXAMPLE IV

A screening program was initiated for the selection of microorganisms capable of converting galactose derivatives and preferably L-galactono-gamma-lactone to L-ascorbic acid. Microorganisms of the genus Candida were selected from the varieties of yeast reported capable of producing enediol compounds.

A large number of Candida species readily available in various culture collections, e.g., American Type Culture Collection, Rockville, Md., Central-Bureau voor Schimmelculture, Delft, Institute Pasteur, Paris and Northern Region Research Lab, Peoria, Ill., were accessed and purified prior to screening studies. The cultures were maintained on G-agar slant tubes or other nutrient media.

A saline suspension of a 24 hour slant of yeast grown on G-agar was employed as the inoculum. A 0.5 ml cell suspension was aseptically added to 50 ml of sterile SM-1 medium (ethanol 1.5% w/v, urea 0.2%) in a 500 ml low actinic Erlenmeyer flask. L-galactano-gamma-lactone (0.5%) was cold sterilized and added to the cooled flasks. The flasks were placed on a rotary shaker and aerated at 200 rpm, 30° C. for 48 hours. The clarified broths were examined for L-ascorbic acid production. The centrifuged, washed cell pastes were treated with 3.0 ml of 10% trichloracetic acid and titrated with 2,6, dichloroindophenol to establish the level of reducing compounds present within the cell. Conversion of L-galactono-gamma-lactone to L-ascorbic acid was observed in the following species, as shown by Table V.

TABLE V

Production of L-Ascorbic Acid (L-$AAH_2$)

| Organism | Source | No # | Micrograms per deciliter | | |
|---|---|---|---|---|---|
| | | | Broth | Cells | Total |
| C. ingens | CBS | 4603 | 350 | 3717 | 4067 |
| C. truncata | CBS | 1899 | 2730 | 5691 | 8421 |
| C. lusitaniae | CBS | 4413 | 1820 | 2100 | 3920 |
| C. berthetii | ATCC | 18808 | 1330 | 2394 | 3724 |
| C. maltusa | ATCC | 20184 | 630 | 1470 | 2100 |
| C. langeronii | ATCC | 22972 | 910 | 1386 | 2296 |
| C. parapsilosis | ATCC | 22019 | 140 | 462 | 602 |
| C. maltosa | ATCC | 28140 | 560 | 1764 | 2324 |
| C. silvae | ATCC | 22685 | 70 | 168 | 238 |
| C. reukaufii | CBS | 611 | 0 | 147 | 147 |
| | RDICC | 5506 | 9660 | 7581 | 17241 |
| C. utiliis | NRRL | Y-900 | | | |
| H. anomala | ATCC | 20029 | 1610 | 2961 | 4571 |
| C. utilis | ATCC | 15239 | 11970 | 3402 | 15372 |
| Y. lipolytica | ATCC | 20390 | 280 | 3696 | 3976 |
| Y. lipolytica | ATCC | 8661 | 70 | 3465 | 3535 |
| C. guilliermondii | IP | 47 | 1820 | 798 | 2618 |
| C. zeylanoides | IP | 207 | 0 | 168 | 168 |
| C. pseudotropicalis | IP | 513 | 70 | 168 | 238 |
| C. pelliculosa | IP | 606 | 1750 | 420 | 2170 |
| C. pulcherrima | IP | 622 | 420 | 756 | 1176 |
| C. robusta | IP | 826 | 0 | 231 | 231 |
| T. candida | ATCC | 10539 | 280 | 546 | 826 |
| C. sloofii | ATCC | 22978 | 0 | 147 | 147 |
| C. norvegensis | CBS | 1911 | 10780 | 1113 | 11893 |
| C. amyloanta | NRRL | Y-7784 | 140 | 168 | 308 |
| C. buinensis | NRRL | Y-11706 | 0 | 147 | 147 |
| C. cacaoi | NRRL | Y-7302 | 1960 | 1428 | 3388 |
| C. conglobata | NRRL | Y-1504 | 0 | 147 | 147 |
| C. deformans | NRRL | Y-321 | 70 | 168 | 238 |
| F. fluviotilis | NRRL | Y-7711 | 420 | 546 | 966 |
| C. vinii | NRRL | Y-94 | 4130 | 2520 | 6650 |

EXAMPLE V

Airlift fermentors have several distinct advantages over conventional agitator-driven shaft fermentors. Among these are improved mass transfer of oxygen, reduced power requirements, and a more gentle environment for the cultivation of organisms compared to the high degree of shear present in mechanically agitated fermentors. Because of these features, airlift fermentors are desirably employed on an industrial scale. The following examples illustrate the use of an airlift tower fermentor for the production of Vitamin C using Candida yeast.

A 4.0 liter laboratory scale airlift fermentor was filled with sterile glycine medium, pH 4.1, containing 2.75% w/v ethanol, 0.7% glycine and 0.5% L-galactono-gamma-lactone. The fermentor was inoculated with a 24 hour suspension of the *C. norvegensis* KCC MF-42 cells washed from G-Agar (2.5%) flasks. The viable cell count at 0 hour was $5.5 \times 10^6$. Aeration of the fermentor was adjusted to 1.9 V/V/m which provided a cycle rate of 5.0 $m^{-1}$. After 24 hours at 30° C., the viable cell count rose to $1.1 \times 10^8$, and at 48 hours was $3.0 \times 10^8$, at 72 hours the viable cell count was $2.8 \times 10^8$. The count declined to $1.7 \times 10^8$ after 91 hours of cultivation. A level of 0.72 $GL^{-1}$ of L-ascorbic acid was produced.

EXAMPLE VI

In a similar airlift tower experiment a high cell density fermentation was performed. In this instance a 24 hour wet cell paste of *C. norvegensis* KCC MF-42 was dispersed in the 4.0 liter tower at a level of 100 $GL^{-1}$ in SM-1 medium containing 0.7% glycine and 0.7% L-

Galactono-gamma-lactone. Ethanol was supplied continuously at a level (0.1–0.3%) neither limiting or inhibitory to yeast growth or productivity. Oxygen-enriched aeration was supplied to the fermentor at 1:1 oxygen-air ratio. Total mixed gas volume was 1.7 V/V/min. Under these conditions a dissolved oxygen saturation level of 30% was maintained in the upper section of the tower. After 20 hours of fermentation, L-ascorbic acid was produced at a level of 1.44 $GL^{-1}$.

It will be appreciated from the previous description that in accordance with the present invention, useful new methods, organisms and culture media have been provided for the manufacture of ascorbic acid. While various aspects of the invention have been specifically described with respect to certain specific embodiments, it will be appreciated that various modifications and adaptations will become apparent from the present disclosure, which are within the spirit and scope of the present invention and are intended to be within the scope of the following claims.

What is claimed is:

1. A process for the manufacture of L-ascorbic acid comprising the steps of
   providing an aqueous fermentation medium comprising an L-galactonic substrate selected from the group consisting of L-galactonic acid, lower alkyl L-galactonic acid esters, L-galactono-gamma-lactone and mixtures thereof, and a carbon energy source selected from the group consisting of ethanol, glycerol and mixtures thereof,
   providing in said fermentation medium a microorganism which is overproductive in L-ascorbic acid synthesis from said substrate and which utilizes said carbon energy source, wherein said microorganism is a Candida yeast or an L-ascorbic acid overproductive mutant strain thereof, and
   culturing said microorganism under aerobic conditions to consume said carbon energy source and to accumulate L-ascorbic acid.

2. A process in accordance with claim 1 wherein said carbon energy source comprises ethanol and said L-galactonic substrate comprises L-galactono-gamma-lactone.

3. A process in accordance with claim 1 wherein said aqueous fermentation medium comprises a nitrogen source and appropriate minerals for growth of said microoganism, and further comprises an effective amount of glycine to enhance production of L-ascorbic acid.

4. A process in accordance with claim 3 wherein said aqueous fermentation medium comprises at least about 0.5 weight percent of glycine, based on the total weight of the aqueous fermentation medium, and wherein said medium has a pH in the range of from about 2.5 to about 6.5.

5. A process in accordance with claim 1 wherein said fermentation is carried out under aerobic conditions of at least about 20 percent oxygen saturation.

6. A process in accordance with claim 1 wherein ethanol and the L-galactonic substrate are derived from a dairy by-product lactose source or citrus pectin.

7. A process in accordance with claim 6 wherein whey, whey permeate, or milk permeate is converted to D-galactose and ethanol, wherein said D-galactose is oxidized to D-galacturonic acid, and wherein said D-galacturonic acid is reduced to an L-galactonic acid substrate.

8. A process in accordance with claim 6 wherein D-galacturonic acid is derived from enzymatic hydrolysis of pectin, and wherein said D-galacturonic acid is reduced to provide an L-galactonic acid substrate.

9. A process in accordance with claim 8 wherein D-galacturonic acid is reduced by Raney nickel, platinum or palladium catalyst and gaseous hydrogen to L-galactonic acid.

10. A process in accordance with claim 6 wherein L-galactonic acid is dehydrated to form L-galactono-gamma-lactone.

11. A process in accordance with claim 1 wherein said fermentation is carried out as a batch, continuous, semi-continuous, fed-batch, dialysis or other recycling mode to produce L-ascorbic acid.

12. A process in accordance with claim 1 wherein said microorganism is immobilized or entrapped by means of a suitable substrate.

13. A process in accordance with claim 1 wherein the fermentation medium contains ethanol as the primary carbon source; L-galactono-gamma-lactone and other organic and inorganic constituents in combinations designed to maximize L-ascorbic acid production and minimize formation of other ascorbic acid analogs.

14. A process in accordance with claim 1 wherein recovery of L-ascorbic acid from fermentation broths or buffered solutions is effected by the use of an ion retardation type resin.

15. A process for producing L-ascorbic acid which comprises the steps of providing a fermentation medium comprising ethanol and L-galactano-gamma-lactone, aerobically culturing a yeast of the strain *Candida norvegensis* MF-56 ATCC 20686 in said fermentation medium to consume ethanol and to convert L-galactano-gamma-lactone to L-ascorbic acid.

* * * * *